(12) United States Patent
Feldchtein

(10) Patent No.: US 7,573,020 B1
(45) Date of Patent: Aug. 11, 2009

(54) OPTOELECTRONIC PROBE SYSTEM WITH ALL-OPTICAL COUPLING

(75) Inventor: Felix I. Feldchtein, Cleveland, OH (US)

(73) Assignee: Imalux Corporation, Cleveland, OH (US)

( * ) Notice: Subject to any disclaimer, the term of this patent is extended or adjusted under 35 U.S.C. 154(b) by 20 days.

(21) Appl. No.: 12/015,560

(22) Filed: Jan. 17, 2008

(51) Int. Cl.
*G01B 9/00* (2006.01)
*A61B 6/00* (2006.01)
*A61B 18/22* (2006.01)

(52) U.S. Cl. .................. 250/227.11; 600/182; 600/478
(58) Field of Classification Search ............ 250/227.11; 600/182, 478
See application file for complete search history.

(56) References Cited

U.S. PATENT DOCUMENTS

| | | | | |
|---|---|---|---|---|
| 4,691,386 A | * | 9/1987 | Eumurian et al. | 398/139 |
| 4,730,891 A | * | 3/1988 | Poorman | 385/74 |
| 5,459,570 A | * | 10/1995 | Swanson et al. | 356/479 |
| 5,570,182 A | * | 10/1996 | Nathel et al. | 356/511 |
| 6,175,669 B1 | * | 1/2001 | Colston et al. | 385/12 |
| 6,608,684 B1 | * | 8/2003 | Gelikonov et al. | 356/479 |
| 6,680,779 B2 | * | 1/2004 | Toida | 356/479 |
| 6,950,692 B2 | * | 9/2005 | Gelikonov et al. | 600/473 |
| 6,992,776 B2 | * | 1/2006 | Feldchtein et al. | 356/479 |
| 7,355,688 B2 | * | 4/2008 | Lash et al. | 356/222 |
| 2008/0106792 A1 | * | 5/2008 | Lash et al. | 359/618 |
| 2008/0108886 A1 | * | 5/2008 | Lash et al. | 600/323 |

* cited by examiner

*Primary Examiner*—John R Lee
(74) *Attorney, Agent, or Firm*—Renner, Otto, Boisselle & Sklar, LLP

(57) ABSTRACT

An optoelectronic probe system with all-optical coupling includes an optoelectronic measuring console coupled with an optoelectronic probe via an optical connector. A supplemental optical signal having an operative wavelength other than an operative wavelength of the regular optical part of the optoelectronic measuring console is communicated to the optoelectronic probe along with the output signal from the optoelectronic measuring console. The supplemental optical signal is then selected by a wavelength-division multiplexer, converted to an electrical signal and used for powering respective components of the optoelectronic probe. Auxiliary signals are also used for identification and storing calibration parameters of the optoelectronic probe, counting events, such as number of sessions used, time in use, and the like.

15 Claims, 5 Drawing Sheets

OPTOELECTRONIC PROBE SYSTEM WITH ALL-OPTICAL COUPLING

BACKGROUND OF THE INVENTION

The subject application is directed to a system with all-optical coupling of an optoelectronic probe and an optoelectronic measuring console. In particular, the subject application is directed to an optoelectronic probe system employing all-optical coupling, which allows for a cost effective, safe, and expedient operation of an optoelectronic probe used in optical measurements.

Optoelectronic measuring techniques, such as, for example, spectroscopy implementing reflectance, light-elastic scattering, or fluorescence, and optical imaging, such as confocal microscopy and optical coherence tomography, typically involve the use of an optoelectronic probe to allow for delivering optical radiation to an associated sample.

Conventionally, the architecture of these devices includes an optoelectronic measuring console and a permanently attached or detachable optoelectronic probe, having optical and electrical communication with the optoelectronic measuring console. The optical communication is typically employed using one or more optical fibers, wherein the electrical communication is provided via electrical wires, as known in the art. Such architecture is definitely simple and cost effective, but has several drawbacks.

By way of example, a galvanic electrical contact between an optoelectronic measuring console and an optoelectronic probe, wherein the optoelectronic measuring console typically has hazardous voltages inside, represents a risk of electrical hazard to an operator and/or patient, since the optoelectronic probe is in contact with an operator and, in the case of biomedical use of the device, with the patient tissue. This risk is typically mitigated by appropriate design of the device, at the expense of additional design, manufacture, validation, and regulatory efforts. In particular, probe circuitry can be galvanically insulated from the rest of the optoelectronic measuring console, using optoelectronic type, capacitor-type, or inductive-type means. However, these means bring additional cost and complexity to the device, especially when medical-grade insulation is required.

Combined electro-optical connectors, i.e. having both optical and electrical contacts, are substantially more expensive and frequently inferior in performance in comparison to optical only or electrical only connectors. The use of separate optical and electrical connectors with a subsequent junction device is also known in the art, but the junction device represents additional cost and complexity as well, especially when medical reprocessing is required, such as disinfection or sterilization.

SUMMARY OF THE INVENTION

In accordance with the subject application, there is provided a system for all-optical coupling of an optoelectronic probe and an optoelectronic measuring console.

Further, in accordance with the subject application, there is provided an optoelectronic probe system employing all-optical coupling which allows for a cost effective, safe, and expedient operation of an optoelectronic probe used in optical measurements.

Still further, in accordance with the subject application, there is provided an optoelectronic probe system employing all-optical coupling that complies with medical-grade requirements.

Further, in accordance with one embodiment of the subject application, there is provided an optoelectronic probe system with all-optical coupling comprising an optoelectronic measuring console, optical connector means, and an optoelectronic probe in optical communication with the optoelectronic measuring console via the optical connector means. The optoelectronic probe includes electrically controlled means comprising at least one electrically controlled module which is, preferably, selected from the group consisting of scanning means, identification means, and monitoring means. The optoelectronic probe further includes transforming means placed in the proximal part of the optoelectronic probe. The transforming means is adapted for receiving an output optical signal from the optoelectronic measuring console via the optical connector means. The transforming means includes selecting means and converting means optically coupled with the selecting means. The selecting means is adapted for selecting a first optical signal and a second optical signal from the output optical signal received from the optoelectronic measuring console via the optical connector means. The converting means is adapted for converting at least a part of the first optical signal into an electrical signal. Further included in the optoelectronic probe is first delivering means and second delivering means. The first delivering means is adapted for delivering the electrical signal from the converting means to the electrically controlled means. The second delivering means is adapted for delivering the second optical signal to an associated sample. The transforming means is further adapted for receiving an optical signal returning from an associated sample via the second delivering means. The transforming means is further adapted for supplying an optical signal representative of the optical signal returning from an associated sample to the optoelectronic measuring console via the optical connector means.

In one embodiment of the subject application, the optoelectronic measuring console comprises a regular optical part, a supplemental optical signal source, and mixing means in optical communication with the supplemental optical signal source, with the regular optical part of the optoelectronic measuring console, and with the optical connector means. The supplemental optical signal source has an operative wavelength other than an operative wavelength of the regular optical part of the optoelectronic measuring console. The mixing means is adapted for supplying the output optical signal from the optoelectronic measuring console to the optoelectronic probe via the optical connector means. The output signal is representative of the output optical signal from the regular optical part of the optoelectronic measuring console and of the supplemental optical signal. The first optical signal selected by the selecting means is representative of the supplemental optical signal, wherein the second optical signal selected by the selecting means is representative of the output optical signal from the regular optical part of the optoelectronic measuring console.

Further, in accordance with one embodiment of the subject application, the optoelectronic measuring console further comprises first auxiliary means adapted for receiving and outputting an auxiliary optical signal, and directional means. The mixing means is in optical communication with the supplemental optical signal source and with the first auxiliary means via the directional means. In this embodiment, the output optical signal from the optoelectronic measuring console supplied by the mixing means to the optoelectronic probe via the optical connector means is further representative of the auxiliary optical signal from the first auxiliary means. In this embodiment, the transforming means further comprises second auxiliary means and splitting and directing means.

The selecting means is in optical communication with the second auxiliary means and with the converting means via the splitting and directing means. In this embodiment, the first optical signal selected by the selecting means is further representative of the auxiliary optical signal. In one embodiment, the second auxiliary means comprises at least one module of the electrically controlled means.

The splitting and directing means is adapted for splitting the first optical signal into a first part and a second part, directing the first part of the first optical signal to the converting means and directing the second part of the first optical signal to the second auxiliary means. The splitting and directing means is further adapted for directing an optical signal returning from the second auxiliary means to the selecting means. Preferably, in this embodiment, the selecting means is further adapted for mixing the optical signal returning from an associated sample with the optical signal returning from the second auxiliary means. In this embodiment, the optical signal being supplied by the transforming means to the optoelectronic measuring console via the optical connector means is further representative of the optical signal returning from the second auxiliary means.

Yet further, in accordance with one embodiment of the subject application, the mixing means is further adapted for receiving from the optoelectronic probe an optical signal representative of the optical signal returning from the distal part of the optoelectronic probe and representative of the optical signal returning from the second auxiliary means via the optical connector means The mixing means is further adapted for selecting, from the received optical signal an optical signal representative of the optical signal returning from an associated sample, and selecting an optical signal representative of the optical signal returning from the second auxiliary means. In this embodiment, the mixing means is further adapted for directing the optical signal representative of the optical signal returning from an associated sample, to the regular optical part of the optoelectronic measuring console. The mixing means is further adapted for directing the optical signal representative of the optical signal returning from the second auxiliary means, to the first auxiliary means via the directional means.

In one embodiment of the subject application, the optoelectronic measuring console further comprises power level altering means in communication with the supplemental optical signal source. In this embodiment, the power level altering means is adapted for lowering the power level of the output optical signal of the supplemental optical signal source to a safe level responsive to a disconnection in the optical connector means. The power level altering means is further adapted for adjusting the power level of the output optical signal of the supplemental optical signal source to an operative level responsive to a connection in the optical connector means. In this embodiment, the optoelectronic probe system preferably comprises indicating means adapted for indicating a status of the optical connector means. The indicating means is in communication with the optoelectronic probe and with the power level altering means.

Further, in accordance with an alternate embodiment of the subject application, there is provided an optoelectronic probe system with all-optical coupling comprising an optoelectronic measuring console, two-channel optical connector means, and an optoelectronic probe in optical communication with the optoelectronic measuring console via the two-channel optical connector means. The optoelectronic measuring console includes a regular optical part and a supplemental optical signal source having an operative wavelength other than an operative wavelength of the regular optical part of the optoelectronic measuring console. The optoelectronic probe is adapted for receiving a first optical signal, representative of a supplemental optical signal from the supplemental optical signal source, and receiving a second optical signal from the regular optical part of the optoelectronic measuring console, via corresponding channels of the two-channel optical connector means.

The optoelectronic probe includes electrically controlled means comprising at least one electrically controlled module, which is, preferably, selected from the group consisting of scanning means, identification means, and monitoring means. The optoelectronic probe further includes converting means comprised in the proximal part of the optoelectronic probe and adapted for converting at least a part of the first optical signal received by the optoelectronic probe, into an electrical signal. Further included in the optoelectronic probe is first delivering means and second delivering means. The first delivering means is adapted for delivering the electrical signal from the converting means to the electrically controlled means. The second delivering means is adapted for delivering the second optical signal received by the optoelectronic probe, to the distal part of the optoelectronic probe for operating the optoelectronic probe and delivering the optical signal returning from the distal part of the optoelectronic probe to the optoelectronic measuring console via a corresponding channel of the two-channel optical connector means. In this embodiment, the regular optical part and the supplemental optical signal source of the optoelectronic measuring console are in optical communication with corresponding channels of the two-channel optical connector means.

In another embodiment of the subject application, the optoelectronic measuring console further comprises first auxiliary means adapted for receiving and outputting an auxiliary optical signal, and directional means. The supplemental optical signal source and the first auxiliary means are in optical communication with a corresponding channel of the two-channel optical connector means via the directional means. The directional means is adapted for directing the auxiliary optical signal from the first auxiliary means and the supplemental optical signal to a corresponding channel of the two-channel optical connector means. In this embodiment, the proximal part of the optoelectronic probe further comprises second auxiliary means adapted for receiving and outputting an auxiliary optical signal, and splitting and directing means. The converting means and the second auxiliary means are in optical communication with a corresponding channel of the two-channel optical connector means via the splitting and directing means. In this embodiment, the first optical signal received by the optoelectronic probe, is further representative of the auxiliary optical signal output by the first auxiliary means. The splitting and directing means is adapted for splitting the first optical signal into a first part and a second part, directing the first part of the first optical signal to the converting means and directing the second part of the first optical signal to the second auxiliary means. The splitting and directing means is further adapted for directing an optical signal returning from the second auxiliary means to a corresponding channel of the two-channel optical connector means. The directional means is further adapted for directing the auxiliary optical signal from the second auxiliary means received via a corresponding channel of the two-channel optical connector means, to the first auxiliary means. In one embodiment, the second auxiliary means comprises at least one module of the electrically controlled means.

In one embodiment of the subject application, the optoelectronic measuring console further comprises power level altering means in communication with the supplemental optical signal source. In this embodiment, the power level altering means is adapted for lowering the power level of the output optical signal of the supplemental optical signal source to a safe level responsive to a disconnection in the two-channel optical connector means. The power level altering means is further adapted for adjusting the power level of the output optical signal of the supplemental optical signal source to an operative level responsive to a connection in the two-channel optical connector means. In this embodiment, the optoelectronic probe system preferably comprises indicating means adapted for indicating a status of the two-channel optical connector means. The indicating means is in communication with the optoelectronic probe and with the power level altering means.

Still other aspects of the present invention will become readily apparent to those skilled in this art from the following description wherein there are shown and described preferred embodiments of this subject application, simply by way of illustration of one of the best modes suited for to carry out the subject application. As it will be realized, the subject application is capable of other different embodiments and its several details are capable of modifications in various obvious aspects all without departing from the subject application. Accordingly, the drawings and description will be regarded as illustrative in nature and not as restrictive.

BRIEF DESCRIPTION OF THE DRAWINGS

The accompanying drawings incorporated in and forming a part of the specification, illustrate the present invention, and together with the description serve to explain the principles of the invention.

DETAILED DESCRIPTION OF THE INVENTION

The subject application is directed to a system with all-optical coupling of an optoelectronic probe and an optoelectronic measuring console. In particular, the subject application is directed to an optoelectronic probe system employing all-optical coupling which allows for a cost effective, safe, and expedient operation of an optoelectronic probe used in optical measurements. The subject application is also directed to optoelectronic probe system employing all-optical coupling that complies with medical-grade requirements. The optoelectronic probe is described herein as an optical fiber implementation, which is preferable for use in medical applications, especially in endoscopy, where flexibility of the optical fiber provides convenient access to different tissues and organs, including internal organs via an endoscope. However, the optoelectronic probe is capable of being implemented with the use of bulk optics.

Figure 1:
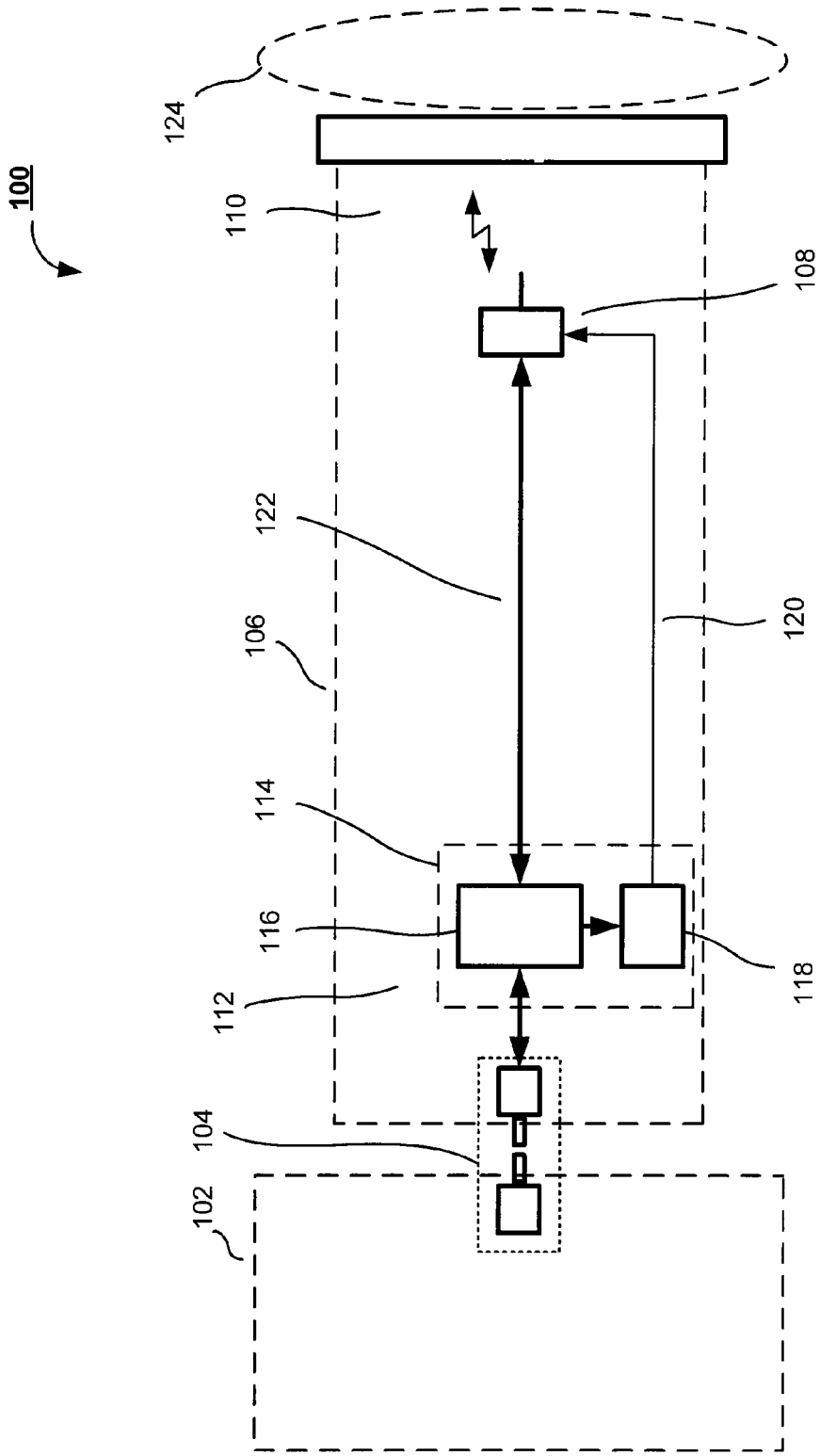
FIG. 1 is a block diagram of an optoelectronic probe system with all-optical coupling according to one embodiment of the subject application.

Turning now to FIG. 1, there is shown a block diagram of an optoelectronic probe system 100 with all-optical coupling according to one embodiment of the subject application. As shown in FIG. 1, the optoelectronic probe system 100 includes an optoelectronic measuring console 102, optical connector means 104, and an optoelectronic probe 106. The optoelectronic probe 106 is in optical communication with the optoelectronic measuring console 102 via the optical connector means 104. As will be recognized by those skilled in the art, the optoelectronic measuring console 102 is any suitable device known in the art used for optical coherence tomography, confocal microscopy, and the like, based on the use of regular reflectance, fluorescent and spectrally encoded microscopy or other optical modalities, as known in the art. A skilled artisan will further appreciate that the optoelectronic probe 106 is any suitable optoelectronic probe known for optical coherence tomography, confocal microscopy applications, and the like, based on the use of regular reflectance, fluorescent and spectrally encoded microscopy, or other optical modalities, as known in the art, modified in accordance with the subject application, as described in detail below. The optical connector means 104 is capable of being implemented, for example and without limitation, as a suitable fiber optic connector with a push-pull latching mechanism which provides quick insertion and removal while also ensuring a positive connection, such as, for example, a LC or SC adapter/connector.

The optoelectronic probe 106 includes electrically controlled means comprising an electrically controlled module 108. As depicted in FIG. 1, the electrically controlled module 108 is comprised in a distal part 110 of the optoelectronic probe 106. In another embodiment, which is not shown in the drawing, one or more electrically controlled modules of the electrically controlled means are capable of being placed in a proximal part 112 of the optoelectronic probe 106. Those skilled in the art will recognize that the electrically controlled means is capable of including several modules, some of which are positioned in the proximal part 112 and others in the distal part 110 of the optoelectronic probe 106. This embodiment is not shown in the FIG. 1.

As will be further appreciated by those skilled in the art, the electrically controlled means is capable of being implemented as scanning means, identification means, and monitoring means, as will be described in detail below. Illustrated in FIG. 1, is an embodiment, in which the electrically controlled module 108 of the electrically controlled means is implemented as a pass-through lateral scanner of an optical coherence tomography device. It will be appreciated that other implementations of the electrically controlled means are equally capable of being used in the optoelectronic probe system 100 without departing from the scope of the subject application. The optoelectronic probe 106 further includes transforming means 114 placed in the proximal part 112 of the optoelectronic probe 106. The transforming means 114 is adapted for receiving an output optical signal from the optoelectronic measuring console 102 via the optical connector means 104. The transforming means 114 includes selecting means 116 and converting means 118 optically coupled with the selecting means 116. The selecting means 116 is adapted for selecting a first optical signal and a second optical signal from the output optical signal received from the optoelectronic measuring console 102 via the optical connector means 104. With respect to the embodiment of FIG. 1, in one embodiment, the selecting means 116 is capable of being implemented as a suitable splitting device, such as for example and without limitation, an optical fiber splitter. In another embodiment, the selecting means 116 is capable of being implemented as a wavelength-division multiplexer, as will be explained in detail below. The converting means 118 is adapted for converting at least a part of the first optical signal into an electrical signal, and is capable of being implemented, for example and without limitation, as a photovoltaic element, such as a suitable photodiode. Further included in the optoelectronic probe 106 is first delivering means 120 and second delivering means 122. The first delivering means 120 is adapted for delivering the electrical signal from the converting means 118 to the electrically controlled module 108. As will be appreciated by a skilled artisan, the first delivering means 120 is capable of being implemented as suitable electric wiring, as known in the art.

The second delivering means 122 is adapted for delivering the second optical signal to the distal part 110 of the optoelectronic probe 106. The second delivering means 122 is capable of being implemented as a suitable optical fiber, as known in the art. It will be appreciated that the second optical signal is used for operating the optoelectronic probe 106, such as for delivering the second optical signal to an associated sample 124, as will be explained in greater detail below. The transforming means 114 is further adapted for receiving an optical signal returning from the distal part 110 of the optoelectronic probe 106 via the second delivering means 122. The transforming means 114 is further adapted for supplying an optical signal representative of the optical signal returning from the distal part 110 of the optoelectronic probe 106, i.e. from an associated sample 124, to the optoelectronic measuring console 102 via the optical connector means 104.

Figure 2:
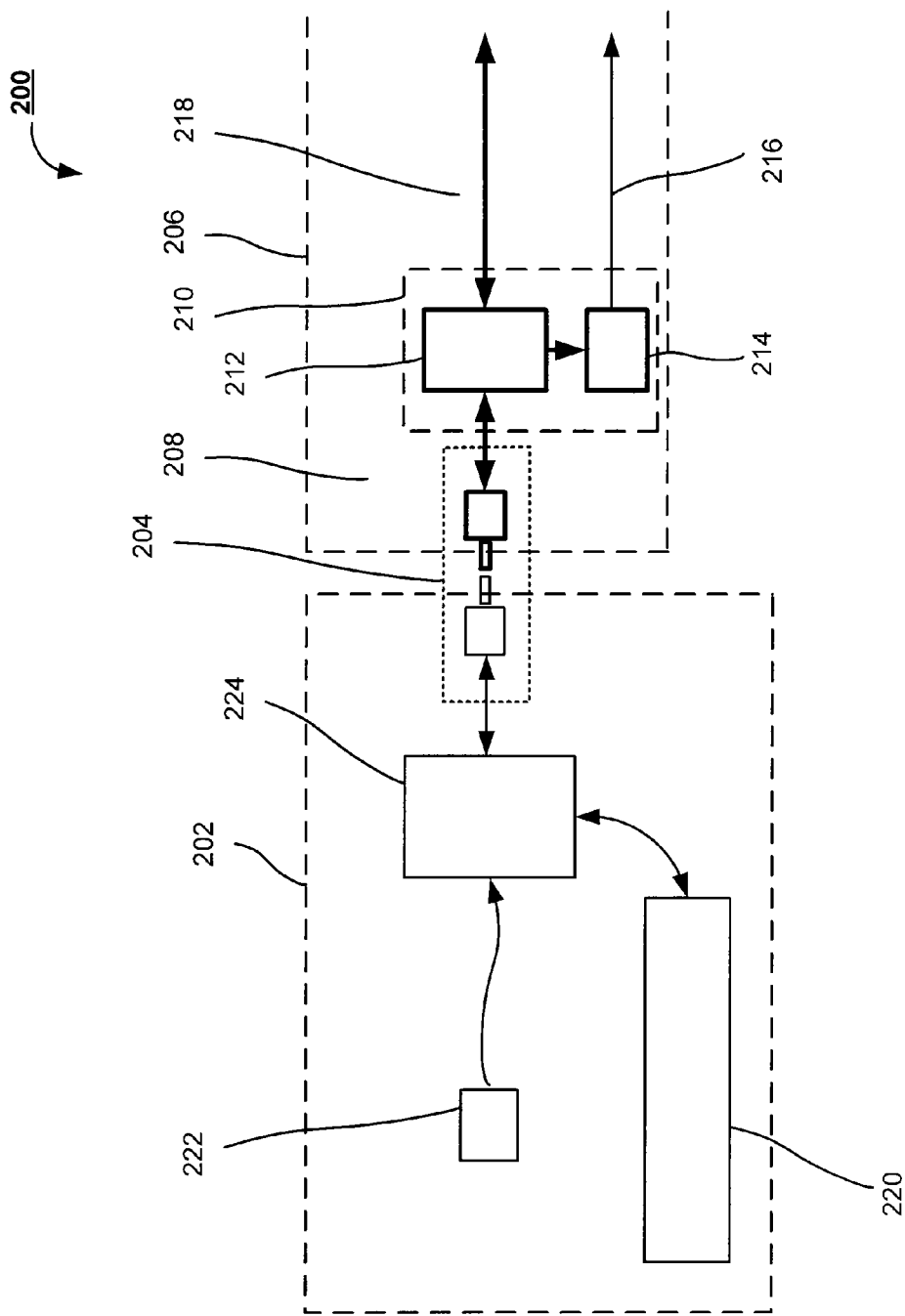
FIG. 2 is a block diagram of an optoelectronic probe system with all-optical coupling according to another embodiment of the subject application.

Turning now to FIG. 2, there is shown a block diagram of an optoelectronic probe system 200 with all-optical coupling according to another embodiment of the subject application. In this embodiment, the system 200 includes an optoelectronic measuring console 202, optical connector means 204, and an optoelectronic probe 206. The optoelectronic probe 206 is in optical communication with the optoelectronic measuring console 202 via the optical connector means 204. In this embodiment, as will be recognized by those skilled in the art, the optoelectronic measuring console 202 is any suitable device known in the art used for optical coherence tomography, confocal microscopy, and the like, based on the use of regular reflectance, fluorescent and spectrally encoded microscopy, or other optical modalities, modified in accordance with the subject application, as described in detail below. A skilled artisan will further appreciate that the optoelectronic probe 206 is any suitable optoelectronic probe known for use in optical coherence tomography, confocal microscopy applications, and the like, based on the use of regular reflectance, fluorescent and spectrally encoded microscopy, or other optical modalities, as known in the art, modified in accordance with the subject application, as described in detail below. The optical connector means 204 is capable of being implemented analogous to the optical connector means 104 described with respect to the embodiment of FIG. 1.

Thus, the optoelectronic probe 206 includes electrically controlled means comprised in a distal part of the optoelectronic probe 206 (not shown in the drawing) and transforming means 210 placed in a proximal part 208 of the optoelectronic probe 206. It will be appreciated by those skilled in the art that the electrically controlled means is capable of being implemented analogous to that described with respect to the embodiment of FIG. 1. As will be further recognized, illustrated in FIG. 2 is the proximal part 208 of the optoelectronic probe 206. The transforming means 210 includes selecting means 212 and converting means 214 optically coupled with the selecting means 212. As will be recognized by those skilled in the art, the selecting means 212 and the converting means 214 are capable of being implemented analogous to, respectively, the selecting means 116 and converting means 118 described above with respect to the embodiment of FIG. 1. Further included in the optoelectronic probe 206 is first delivering means 216 and second delivering means 218. As will be appreciated by those skilled in the art, the first delivering means 216 and second delivering means 218 are adapted to perform analogous functions as corresponding means in the embodiment of FIG. 1, and are capable of being implemented analogous to that described with respect to the embodiment of FIG. 1.

As shown in FIG. 2, the optoelectronic measuring console 202 comprises a regular optical part 220, a supplemental optical signal source 222, and mixing means 224. The regular optical part 220 is any suitable device known in the art used for optical coherence tomography, confocal microscopy, and the like, based on the use of regular reflectance, fluorescent and spectrally encoded microscopy or other optical modalities, as known in the art. The supplemental optical signal source 222 is capable being implemented, for example and without limitation, as a diode laser. The mixing means 224 is capable of being implemented analogous to the transforming means 210, such as a wave division multiplexer, as known in the art. The mixing means 224 is in optical communication with the supplemental optical signal source 222, with the regular optical part 220 of the optoelectronic measuring console 202, and with the optical connector means 204. The supplemental optical signal source 222 has an operative wavelength other than an operative wavelength of the regular optical part 220 of the optoelectronic measuring console 202. For example and without limitation, the operative wavelength of the regular optical part 220 of the optoelectronic measuring console 202 is capable of being 1300 nm, wherein the operative wavelength of the supplemental optical signal source 222 is capable of being 1550 nm. The mixing means 224 is adapted for supplying the output optical signal from the optoelectronic measuring console 202 to the optoelectronic probe 206 via the optical connector means 204 and is capable of being implemented, for example an without limitation, as a wavelength-division multiplexer. The output signal of the optoelectronic measuring console 202, is representative of the output optical signal from the regular optical part 220 and of the supplemental optical signal. The selecting means 212 of the optoelectronic probe 206 is adapted for selecting a first optical signal and a second optical signal from the output optical signal received from the optoelectronic measuring console 202 via the optical connector means 204. In this embodiment, the first optical signal selected by the selecting means is representative of the supplemental optical signal, wherein the second optical signal selected by the selecting means 212 is representative of the output optical signal from the regular optical part 220 of the optoelectronic measuring console 202.

In accordance with another embodiment of the subject application, the optoelectronic probe system 200 is capable of further including power level altering means (not shown in the drawings). The power level altering means is comprised in the optoelectronic measuring console 202 in communication with the supplemental optical signal source 222. The power level altering means is adapted for lowering the power level of the output optical signal of the supplemental optical signal source 222 to a safe level responsive to a disconnection in the optical connector means 204. The power level altering means is further adapted for adjusting the power level of the output optical signal of the supplemental optical signal source 222 to an operative level responsive to a connection in the optical connector means 204. This embodiment, preferably, further comprises indicating means (not shown in FIG. 1) adapted for indicating a status of the optical connector means 204. The indicating means is in communication with the optoelectronic probe 206 and with the power level altering means. Those skilled in the art will appreciate that the power level altering means and the indicating means are capable of being implemented as any suitable means known in the art. To detect the connection of the optoelectronic probe 206 a variety of means are capable of being used, as known in the art. They include, for example and without limitation, mechanical activation of an electrical switch inside the optoelectronic measuring console 202; measuring of light reflection from the optical connector means 204, the latter being known to change as the optoelectronic probe 206 is connected or disconnected to the optoelectronic measuring console 202. Another way of detecting connection and disconnection of the optoelectronic probe 206 is using communication between the first and second auxiliary means, as will be explained below with reference to the embodiment of FIG. 3.

Figure 3:
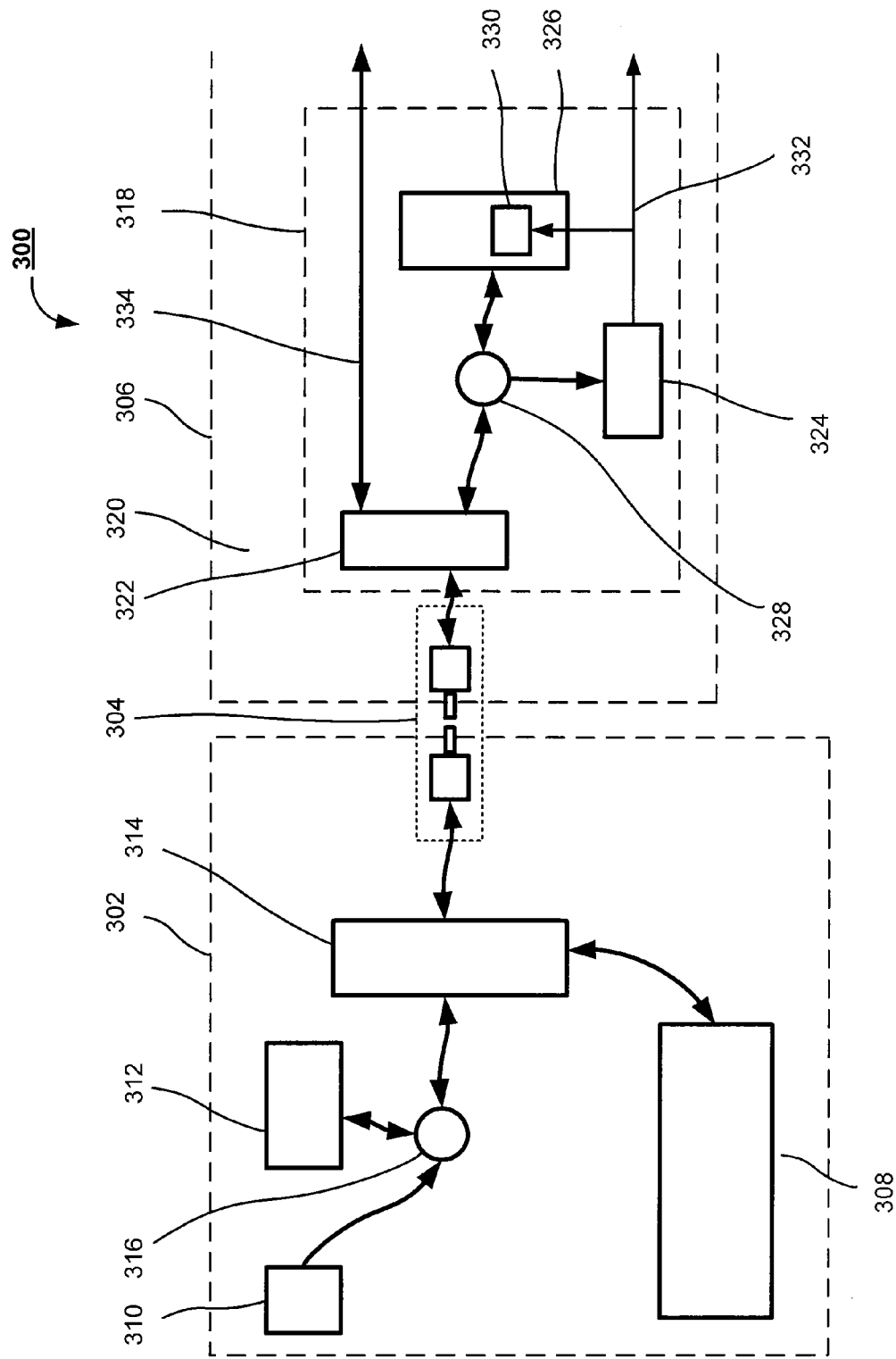
FIG. 3 is a block diagram of an optoelectronic probe system with all-optical coupling according to another embodiment of the subject application.

Turning now to FIG. 3, there is shown a block diagram of an optoelectronic probe system 300 with all-optical coupling according to another embodiment of the subject application. The system 300 includes an optoelectronic measuring console 302, optical connector means 304, and an optoelectronic probe 306. The optoelectronic probe 306 is in optical communication with the optoelectronic measuring console 302 via the optical connector means 304. In this embodiment, as will be recognized by those skilled in the art, the optoelectronic measuring console 302 is any suitable device known in the art used for optical coherence tomography, confocal microscopy, and the like, based on the use of regular reflectance, fluorescent and spectrally encoded microscopy, or other optical modalities, modified in accordance with the subject application, as described in detail below. A skilled artisan will further appreciate that the optoelectronic probe 306 is any suitable optoelectronic probe known for optical coherence tomography, confocal microscopy applications, and the like, based on the use of regular reflectance, fluorescent and spectrally encoded microscopy, or other optical modalities, as known in the art, modified in accordance with the subject application, as described in detail below.

In this embodiment, the optoelectronic measuring console 302 includes a regular optical part 308, a supplemental optical signal source 310, first auxiliary means 312, mixing means 314, and directional means 316. As will be appreciated, the regular optical part 308 is any suitable device known in the art used for optical coherence tomography, confocal microscopy, and the like, based on the use of regular reflectance, fluorescent and spectrally encoded microscopy or other optical modalities, as known in the art. The supplemental optical signal source 310 is capable of implementation analogous to that described with respect to the embodiment of FIG. 2. The first auxiliary means 312 is capable of being implemented, for example and without limitation, as an optoelectronic transmitter/receiver combined with a probe identification requesting and reading means and associated electronics, as known in the art. The directional means 316 is capable of being implemented, for example and without limitation, as an optical fiber coupler/splitter, as will be appreciated by those skilled in the art. The mixing means 314 is in optical communication with the optical connector means 304 and is capable of being implemented analogous to the mixing means 224 of the embodiments depicted in FIG. 2. The mixing means 314 is further in optical communication with the supplemental optical signal source 310 and with the first auxiliary means 312 via the directional means 316. The same as in the embodiment referred to in FIG. 2, the supplemental optical signal source 310 has an operative wavelength other than an operative wavelength of the regular optical part 308 of the optoelectronic measuring console 302. The first auxiliary means 312 is adapted for receiving and outputting an auxiliary optical signal, as will be described in greater detail below. The optical connector means 304 is capable of being implemented analogous to the optical connector means 104 described with respect to the embodiment of FIG. 1.

The optoelectronic probe 306 includes an electrically controlled module comprised in a distal part of the optoelectronic probe 306 (not shown in the drawing) and transforming means 318 placed in a proximal part 320 of the optoelectronic probe 306. As will be recognized, illustrated in FIG. 3 is the proximal part 320 of the optoelectronic probe 306. The transforming means 318 includes selecting means 322, converting means 324, second auxiliary means 326, and splitting and directing means 328. The selecting means 322 is in optical communication with the second auxiliary means 326 and with the converting means 324 via the splitting and directing means 328. The selecting means 322 is capable of implementation analogous to the selecting means 212 of the embodiment depicted in FIG. 2. In the embodiment of FIG. 3, the second auxiliary means 326 comprises an electrically controlled module 330. The splitting and directing means 328 is capable of being implemented as, for example and without limitation, as an optical fiber coupler, as known in the art. Those skilled in the art will recognize that the electrically controlled module 330 is capable of implementation, for example and without limitation, as an identification module, monitoring module, and the like. Further included in the optoelectronic probe 306 is first delivering means 332 and second delivering means 334. The first delivering means 332 is adapted for delivering the electrical signal from the converting means 324 to the module of the electrically controlled means positioned in the distal part of the optoelectronic probe 306 (not shown). The first delivering means 332 is further adapted for delivering the electrical signal from the converting means 324 to the electrically controlled module 330. As will be appreciated by a skilled artisan, the first delivering means 332 is capable of being implemented as suitable electric wiring, as known in the art.

The second delivering means 334 is adapted for delivering the second optical signal to the distal part (not shown) of the optoelectronic probe 306. The second delivering means 334 is capable of being implemented as a suitable optical fiber, as known in the art. It will be appreciated that the second optical signal is used for operating the optoelectronic probe 306, such as for delivering the second optical signal to an associated sample (not shown in FIG. 3), as will be explained in greater detail below. The selecting means 322 is adapted for selecting a first optical signal and a second optical signal from the output optical signal received from the optoelectronic measuring console 302 via the optical connector means 304. In this embodiment, the first optical signal selected by the selecting means 322 is representative of the supplemental optical signal and is representative of the auxiliary optical signal.

The second optical signal selected by the selecting means 322 is representative of the output optical signal from the regular optical part 308 of the optoelectronic measuring console 302. The splitting and directing means 328 is adapted for splitting the first optical signal into a first part and a second part, directing the first part of the first optical signal to the converting means 324, and directing the second part of the first optical signal to the second auxiliary means 326. The splitting and directing means 328 is further adapted for directing an optical signal returning from the second auxiliary means 326 to the selecting means 322. In this embodiment, the selecting means 322 is further adapted for mixing the optical signal returning from an associated sample with the optical signal returning from the second auxiliary means 326. In this embodiment, the optical signal being supplied by the transforming means 318 to the optoelectronic measuring console 302 via the optical connector means 304 is representative of the optical signal returning from an associated sample, and representative of the optical signal returning from the second auxiliary means 326.

Further, in this embodiment of the subject application, the mixing means 314 is further adapted for receiving from the optoelectronic probe 306, an optical signal supplied by the transforming means 318 via the optical connector means 304. The mixing means 314 is further adapted for selecting, from the received optical signal an optical signal representative of the optical signal returning from an associated sample, and selecting an optical signal representative of an optical signal returning from the second auxiliary means 326. In this embodiment, the mixing means 314 is further adapted for directing the optical signal representative of the optical signal returning from an associated sample, to the regular optical part 308 of the optoelectronic measuring console 302. The mixing means 314 is further adapted for directing the optical signal representative of the optical signal returning from the second auxiliary means 326, to the first auxiliary means 312 via the directional means 316.

Figure 4:
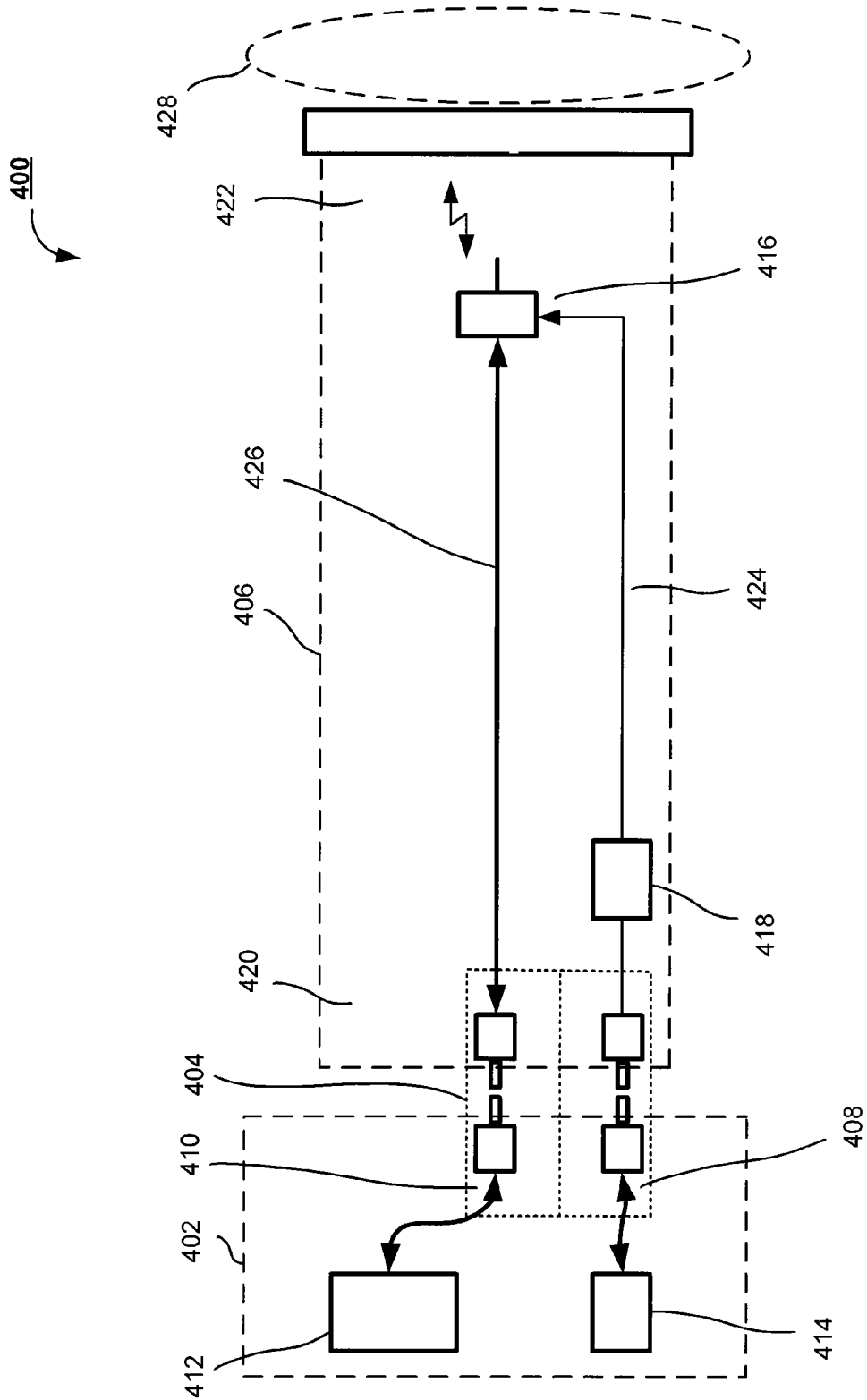
FIG. 4 is a block diagram of an optoelectronic probe system with all-optical coupling according to another embodiment of the subject application.

Turning now to FIG. 4, there is shown a block diagram of an optoelectronic probe system 400 with all-optical coupling according to another embodiment of the subject application. The optoelectronic probe system 400, as shown in FIG. 4, includes an optoelectronic measuring console 402, two-channel optical connector means 404, and an optoelectronic probe 406 in optical communication with the optoelectronic measuring console 402 via the two-channel optical connector means 404. In this embodiment, as will be recognized by those skilled in the art, the optoelectronic measuring console 402 is any suitable device known in the art used for optical coherence tomography, confocal microscopy, and the like, based on the use of regular reflectance, fluorescent and spectrally encoded microscopy, or other optical modalities, modified in accordance with the subject application, as described in detail below. A skilled artisan will further appreciate that the optoelectronic probe 406 is any suitable optoelectronic probe known for optical coherence tomography, confocal microscopy applications, and the like, based on the use of regular reflectance, fluorescent and spectrally encoded microscopy, or other optical modalities, as known in the art, modified in accordance with the subject application, as described in detail below. The two-channel optical connector means 404 is capable of being implemented, for example and without limitation, as a suitable double fiber optic connector with a push-pull latching mechanism which provides quick insertion and removal while also ensuring a positive connection, such as, for example, a double LC or SC adapter/connector. As depicted in FIG. 4, the two-channel optical connector means 404 includes a channel 408 and a channel 410.

The optoelectronic measuring console 402 includes a regular optical part 412 and a supplemental optical signal source 414. The regular optical part 412 is any suitable device known in the art used for optical coherence tomography, confocal microscopy, and the like, based on the use of regular reflectance, fluorescent and spectrally encoded microscopy or other optical modalities, as known in the art. As will be appreciated by those skilled in the art, the supplemental optical signal source 414 is capable of having an operative wavelength other or the same as an operative wavelength of the regular optical part 412 of the optoelectronic measuring console 402. It will be recognized that the supplemental optical signal source 414 is capable of being implemented analogous to the supplemental optical signal source 222 described above with respect to the embodiment of FIG. 2. As shown in FIG. 4, the regular optical part 412 and the supplemental optical signal source 414 of the optoelectronic measuring console 402 are in optical communication with corresponding channels 410, 408, respectively, of the two-channel optical connector means 404. The optoelectronic probe 406 is adapted for receiving a first optical signal, representative of a supplemental optical signal from the supplemental optical signal source 414, and receiving a second optical signal from the optoelectronic measuring console 402 via corresponding channels 408, 410 of the two-channel optical connector means 404. The optoelectronic probe 406 includes electrically controlled means comprising an electrically controlled module 416 and converting means 418 comprised in a proximal part 420 of the optoelectronic probe 406.

The electrically controlled module 416 is capable of being comprised in the proximal part 420 or in a distal part 422 of the optoelectronic probe 406. As will be recognized, FIG. 4 illustrates an embodiment, in which the electrically controlled module 416 is comprised in the distal part 422 of the optoelectronic probe 406. Those skilled in the art will recognize that the electrically controlled means is capable of including several modules, some of which are positioned in the proximal part 420 and others in the distal part 422 of the optoelectronic probe 406. As will be further appreciated, illustrated in FIG. 4, is an embodiment, in which the electrically controlled module 416 of the electrically controlled means is implemented as a pass-through lateral scanner of an optical coherence tomography device. It will be appreciated that other implementations of the electrically controlled means are equally capable of being used in the optoelectronic probe system 400 without departing from the scope of the subject application. The converting means 418 is adapted for converting the first optical signal received by the optoelectronic probe 406, into an electrical signal and is capable of being implemented analogous to the converting means 118 described above with respect to the embodiment of FIG. 1. Further included in the optoelectronic probe 406 is first delivering means 424 and second delivering means 426. The first delivering means 424 is adapted for delivering the electrical signal from the converting means 418 to the electrically controlled module 416. As will be appreciated by a skilled artisan, the first delivering means 424 is capable of being implemented as suitable electric wiring, as known in the art.

The second delivering means 426 is adapted for delivering the second optical signal to the distal part 422 of the optoelectronic probe 406 for operating the optoelectronic probe 406. The second delivering means 426 is capable of being implemented as a suitable optical fiber, as known in the art. It will be appreciated that the second optical signal is used for operating the optoelectronic probe 406, such as delivering the second optical signal to an associated sample 428, as will be explained in greater detail below. The second delivering means 426 is further adapted for delivering the optical signal returning from an associated sample 428 to the optoelectronic measuring console 402 via a corresponding channel of the two-channel optical connector means 404.

Figure 5:
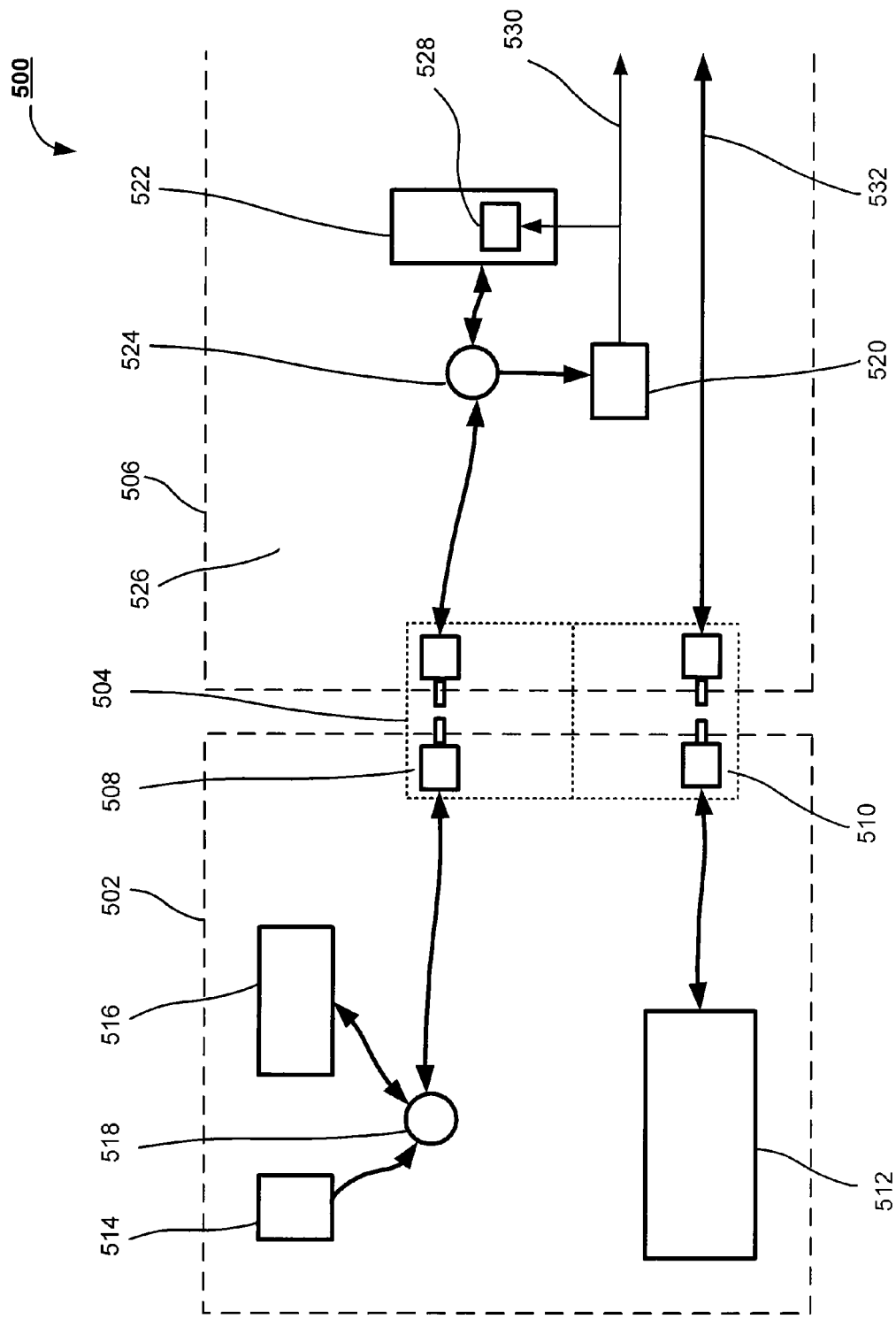
FIG. 5 is a block diagram of an optoelectronic probe system with all-optical coupling according to another embodiment of the subject application.

Referring now to FIG. 5, there is shown a block diagram of an optoelectronic probe system 500 with all-optical coupling according to another embodiment of the subject application. The optoelectronic probe system 500, as shown in FIG. 5, includes an optoelectronic measuring console 502, two-channel optical connector means 504, and an optoelectronic probe 506 in optical communication with the optoelectronic measuring console 502 via the two-channel optical connector means 504. In this embodiment, as will be recognized by those skilled in the art, the optoelectronic measuring console 502 is any suitable device known in the art used for optical coherence tomography, confocal microscopy, and the like, based on the use of regular reflectance, fluorescent and spectrally encoded microscopy, or other optical modalities, modified in accordance with the subject application, as described in detail below. A skilled artisan will further appreciate that the optoelectronic probe 506 is any suitable optoelectronic probe known for optical coherence tomography, confocal microscopy applications, and the like, based on the use of regular reflectance, fluorescent and spectrally encoded microscopy, or other optical modalities, as known in the art, modified in accordance with the subject application, as described in detail below. It will be appreciated that the two-channel optical connector means 504 is capable of being implemented, for example and without limitation, analogous to the two-channel optical connector means 404 of the embodiment shown in FIG. 4. As depicted in FIG. 5, the two-channel optical connector means 504 includes a channel 508 and a channel 510.

In this embodiment, the optoelectronic measuring console 502 includes a regular optical part 512, a supplemental optical signal source 514, first auxiliary means 516, and directional means 518. The regular optical part 512 is any suitable device known in the art used for optical coherence tomography, confocal microscopy, and the like, based on the use of regular reflectance, fluorescent and spectrally encoded microscopy or other optical modalities, as known in the art. The regular optical part 512 is in optical communication with the corresponding channel 510 of the two-channel optical connector means 504. The supplemental optical signal source 514 and the first auxiliary means 516 are in optical communication with the corresponding channel 508 of the two-channel optical connector means 504 via the directional means 518. The supplemental optical signal source 514 and the first auxiliary means 516 are capable of implementation as corresponding means described above with respect to the embodiment of FIG. 3. The directional means 518 is capable of being implemented analogous to the directional means 316 of the embodiment depicted in FIG. 3. The directional means 518 is adapted for directing the auxiliary optical signal from the first auxiliary means 516 and the supplemental optical signal from the source 514 to the corresponding channel 508 of the two-channel optical connector means 504. The same as in the embodiment referred to in FIG. 4, the supplemental optical signal source 514 has an operative wavelength other than an operative wavelength of the regular optical part 512 of the optoelectronic measuring console 502. The first auxiliary means 516 is adapted for receiving and outputting an auxiliary optical signal, as will be described in greater detail below. The optical connector means 504 is capable of being implemented analogous to the optical connector means 404 described with respect to the embodiment of FIG. 4.

The optoelectronic probe 506 comprises electrically controlled means including an electrically controlled module, such as a scanner, placed in a distal part of the optoelectronic probe 506 (not shown in the drawing), converting means 520, second auxiliary means 522, and splitting and directing means 524. As will be recognized, illustrated in FIG. 5 is a proximal part 526 of the optoelectronic probe 506, comprising the converting means 520, the second auxiliary means 522 and the splitting and directing means 524. The converting means 520 and the second auxiliary means 522 are in optical communication with the corresponding channel 508 via the splitting and directing means 524. It will be appreciated that the converting means 520 is capable of being implemented analogous to the converting means 118 described above with respect to the embodiment of FIG. 1, wherein the second auxiliary means 522 is capable of implementation analogous to the second auxiliary means 326 described above with respect to the embodiment of FIG. 3. In the embodiment of FIG. 5, the second auxiliary means 522 comprises an electrically controlled module 528 of the electrically controlled means. Those skilled in the art will recognize that the electrically controlled module 528 is capable of implementation, for example and without limitation, as an identification module, monitoring module, and the like. Further included in the optoelectronic probe 506 is first delivering means 530 and second delivering means 532. As will be appreciated by those skilled in the art, the first delivering means 530 and second delivering means 532 are adapted to perform analogous functions as corresponding means in the embodiments of FIGS. 1 through 4, and are capable of being implemented analogous to that described with respect to the above embodiments. In this embodiment, the first optical signal received by the optoelectronic probe 506 is representative of the supplemental optical signal from the supplemental optical signal source 514 and representative of the auxiliary optical signal output by the first auxiliary means 516.

The splitting and directing means 524 is adapted for splitting the first optical signal into a first part and a second part, directing the first part of the first optical signal to the converting means 520 and directing the second part of the first optical signal to the second auxiliary means 522. The splitting and directing means 524 is further adapted for directing an optical signal returning from the second auxiliary means 522 to the corresponding channel 508 of the two-channel optical connector means 504. The splitting and directing means 524 is capable of implementation analogous to the splitting and directing means 328 described above with respect to the embodiment of FIG. 3. The directional means 518 of the optoelectronic measuring console 502 is further adapted for directing the auxiliary optical signal from the second auxiliary means 522 received via the corresponding channel 508 of the two-channel optical connector means 504 to the first auxiliary means 516.

In accordance with the subject application, the embodiments of the optoelectronic probe system illustrated in FIGS. 3 through 5 are capable of advantageously further including power level altering means and indicating means (not shown in the drawings) analogous to that described above with reference to the embodiment of FIG. 2. As described above, the power level altering means is adapted for lowering the power level of the output optical signal of the corresponding supplemental optical signal source to a safe level responsive to a disconnection of the corresponding optical connector means. The power level altering means is further adapted for adjusting the power level of the output optical signal of the supplemental optical signal source to an operative level responsive to a connection in a corresponding optical connector means.

Further, in accordance with the subject application, the embodiments of the optoelectronic probe system illustrated in FIGS. 1 through 5 are capable of including an electrical energy storage element (not shown in the drawings), such as, for example and without limitation, a capacitor or an accumulator unit placed in the proximal part of the optoelectronic probe, for example in the converting means, or in communication with the converting means. As will be appreciated by those skilled in the art, this energy storage element is adapted for accumulating electrical energy when power consumption for the probe electronics is low and spend it when the power consumption grows high.

Referring now to operation of the optoelectronic probe system with all-optical coupling 100 in accordance with the subject application shown in FIG. 1, the operation of the optoelectronic probe system 100 commences by placing the optoelectronic probe 106 at a predetermined position with respect to the associated sample 124, and providing an optical communication between the optoelectronic probe 106 with the optoelectronic measuring console 102 via the optical connector means 104. An output optical signal from the optoelectronic measuring console 102 is then received by transforming means 114, positioned in the proximal part 112 of the optoelectronic probe 106, via the optical connector means 104. The selecting means 116 of the transforming means 114 selects a first optical signal and a second optical signal from the output optical signal received from the optoelectronic measuring console 102.

In one embodiment with respect to FIG. 1, the output optical signal from the optoelectronic measuring console 102 comprises two wavelengths. A skilled artisan will recognize that the latter is accomplished by the optical source of the optoelectronic measuring console 102 being a two-wavelength optical source, as known in the art. In this embodiment, the selecting means 116 implemented as a wavelength-division multiplexer selects a first optical signal of a first wavelength and a second optical signal of a second wavelength. The converting means 118 then converts the first optical signal into an electrical signal, which is delivered to the electrically controlled module 108, placed in the distal part 110 of the optoelectronic probe 106, via the first delivering means 120. In another embodiment with respect to FIG. 1, the output optical signal from the optoelectronic measuring console 102 comprises one wavelength. In this embodiment, the selecting means 116 implemented as suitable splitting means, splits the output optical signal received from the optoelectronic measuring console 102 in accordance with a predetermined ratio into a first optical signal and a first optical signal. The converting means 118 then converts the first optical signal into an electrical signal, which delivered to the electrically controlled module 108, as described above.

The second delivering means 122 delivers the second optical signal from the selecting means 116 to the distal part 110 for operating the optoelectronic probe 106. As will be appreciated by a skilled artisan, the second optical signal is delivered to an associated sample 124. Those skilled in the art will further recognize that the second optical signal is reflected or backscattered from the associated sample 124 and an optical signal returning from an associated sample 124 is then delivered via the second delivering means 122 to the transforming means 114. Next, the transforming means 114 supply the optical signal returning from an associated sample 124 to the optoelectronic measuring console 102 via the optical connector means 104.

Referring now to operation of the optoelectronic probe system with all-optical coupling 200 in accordance with the subject application shown in FIG. 2, the operation of the optoelectronic probe system 200 commences analogous to that described with respect to the embodiment of FIG. 1. Thus, the operation of the optoelectronic probe system 200 commences by placing the optoelectronic probe 206 at a predetermined position with respect to the associated sample (not shown in the drawing), and providing an optical communication between the optoelectronic probe 206 with the optoelectronic measuring console 202 via the optical connector means 204. A supplemental optical signal is then generated by the supplemental optical signal source 222, which is mixed in the mixing means 224 with the optical signal from the regular optical part 220 of the optoelectronic measuring console 202.

The mixing means 224 then supplies an output signal to the optoelectronic probe 206 via the optical connector means 204. The output signal is representative of the output optical signal from the regular optical part 220 of the optoelectronic measuring console 202 and of the supplemental optical signal source 222. As mentioned above, the supplemental optical signal source 222 has an operative wavelength other than an operative wavelength of the regular optical part 220 of the optoelectronic measuring console 202. The selecting means 212 of optoelectronic probe 206 then selects a first optical signal representative of the supplemental optical signal, and a second optical signal representative of the output optical signal from the regular optical part 220 of the optoelectronic measuring console 202. The converting means 214 then converts the first optical signal into an electrical signal, which is delivered to the electrically controlled means (not shown) via the first delivering means 216, analogous to that described above with respect to the embodiment of FIG. 1. The second delivering means 218 delivers the second optical signal from the selecting means 212 to an associated sample (not shown) for operating the optoelectronic probe 206. As will be recognized by those skilled in the art, further operation of the optoelectronic probe system 200 is analogous to that described with respect to the embodiment of FIG. 1.

In one embodiment of the subject application, in an event of a disconnection of the optical connector means 204, a signal from the indicating means is communicated to the power level altering means (not shown in the drawing). The power level altering means then lowers the power of the output optical signal of the supplemental optical signal source 222 to a safe level. As will be appreciated by a skilled artisan, when the connection of the optical connector means 204 is restored, the power level altering means adjusts the power of the output optical signal of the supplemental optical signal source 222 to an operative level.

Referring now to operation of the optoelectronic probe system with all-optical coupling 300 in accordance with the subject application shown in FIG. 3, the operation of the optoelectronic probe system 300 commences analogous to that described with respect to the embodiments of FIG. 1 and FIG. 2. A supplemental optical signal is then generated by the supplemental optical signal source 310, and an auxiliary optical signal is generated by the first auxiliary means 312. The supplemental optical signal and the auxiliary optical signal are then mixed in the mixing means 314 with the optical signal from the regular optical part 308 of the optoelectronic measuring console 302. The mixing means 314 then supplies the output signal of the optoelectronic measuring console 302 to the optoelectronic probe 306 via the optical connector means 304. As will be appreciated by a skilled artisan, the output signal of the optoelectronic measuring console 302 is representative of the of the output optical signal from the regular optical part 308 of the optoelectronic measuring console 302, of the supplemental optical signal from the source 310, and representative of the optical signal output by the first auxiliary means 312. The selecting means 322 selects a first optical signal representative of the supplemental optical signal from the source 310, and of the optical signal output by the first auxiliary means 312. The selecting means 322 also selects a second optical signal representative of the of the output optical signal from the regular optical part 308 of the optoelectronic measuring console 302. The second delivering means 334 then delivers the second optical signal from the selecting means 322 to the associated sample (not shown) for operating the optoelectronic probe 306.

The splitting and directing means 328 splits the first optical signal into a first part and second part, directs the first part of the first optical signal to the converting means 324, and directs the second part of the first optical signal to the second auxiliary means 326. The first delivering means 332 then delivers the electrical signal from the converting means 324 to the electrically controlled module 330 comprised in the second auxiliary means 326, and to the electrically controlled module comprised in the distal part of the optoelectronic probe, such as described with respect to the embodiment of FIG. 1. The splitting and directing means 328 then directs an optical signal returning from the second auxiliary means 326 to the selecting means 322. The selecting means 322 then provides mixing of the optical signal returning from an associated sample via the second delivering means 334, with the optical signal returning from the second auxiliary means 326. The transforming means 318 then supplies the mixed optical signal to the optoelectronic measuring console 302 via the optical connector means 304, which mixed optical signal is representative of the of the optical signal returning from an associated sample and representative of the optical signal returning from the second auxiliary means 326.

Next, the mixing means 314 receive from the optoelectronic probe 306 an optical signal supplied by the transforming means 318 via the optical connector means 304. The mixing means 314 then selects from the received optical signal, an optical signal representative of the optical signal returning from an associated sample, and selects an optical signal representative of an auxiliary optical signal returning from the second auxiliary means 326. The mixing means 314 then directs the optical signal representative of the optical signal returning from an associated sample, to the regular optical part 308 of the optoelectronic measuring console 302. The optical signal representative of the optical signal returning from the second auxiliary means 326 is directed by the mixing means 314 to the first auxiliary means 312 via the directional means 316.

As will be recognized by those skilled in the art, the second auxiliary means 326 is capable of providing a unique identification of the optoelectronic probe 306, storing calibration parameters of the optoelectronic probe 306, counting events, such as number of sessions used, time in use, and the like, and communicating this information to the optoelectronic measuring console 302, as described in detail above.

Referring now to operation of the optoelectronic probe system with all-optical coupling 400 in accordance with the subject application shown in FIG. 4, the operation of the optoelectronic probe system 400 commences analogous to that described with respect to the embodiments of FIGS. 1 through 3. A supplemental optical signal is then generated by the supplemental optical signal source 414 comprised in the optoelectronic measuring console 402. The supplemental optical signal and the output signal from the regular part 412 of the optoelectronic measuring console 402 are communicated to the optoelectronic probe 406 via the corresponding channels 408, 410, respectively, of the two-channel optical connector means 404. The optoelectronic probe 406 receives the first optical signal, representative of a supplemental optical signal from the supplemental optical signal source 414, and receives the second optical signal from the optoelectronic measuring console 402 via corresponding channels 408, 410 of the two-channel optical connector means 404. The converting means 418 then converts the first optical signal into an electrical signal, which is delivered to the electrically controlled module 416 via the first delivering means 424, analogous to that described above with respect to the embodiment of FIG. 1. The second delivering means 426 delivers the second optical signal received by the optoelectronic probe 406 to an associated sample 428 for operating the optoelectronic probe 406. As will be recognized by those skilled in the art, further operation of the optoelectronic probe system 400 is analogous to that described with respect to the embodiment of FIG. 1.

Referring now to operation of the optoelectronic probe system with all-optical coupling 500 in accordance with the subject application shown in FIG. 5, the operation of the optoelectronic probe system 500 commences analogous to that described with respect to the embodiments of FIGS. 1 through 4. A supplemental optical signal is then generated by the supplemental optical signal source 514 comprised in the optoelectronic measuring console 502, and an auxiliary optical signal is generated by the first auxiliary means 516. The supplemental optical signal and the auxiliary optical signal are then directed by the directional means 518 as a first optical signal to the optoelectronic probe 506 via the corresponding channel 508 of the optical connector means 504. The optical signal from the regular part 512 of the optoelectronic measuring console 502, which is a second optical signal, is communicated to the optoelectronic probe 506 via the corresponding channel 510 of the optical connector means 504. The second delivering means 532 then delivers the second optical signal from the optical connector means 504 to an associated sample (not shown) for operating the optoelectronic probe 506, and thereinafter delivers an optical signal returning from an associated sample to the regular part 512 of the optoelectronic measuring console 502 via the corresponding channel 510.

As will be appreciated by a skilled artisan, the first optical signal received by the optoelectronic probe 506 via the channel 508 is representative of the supplemental optical signal from the source 514, and representative of the optical signal output by the first auxiliary means 516. The splitting and directing means 524 then splits the first optical signal into a first part and second part, directs the first part of the first optical signal to the converting means 520, and directs the second part of the first optical signal to the second auxiliary means 522. The first delivering means 530 then delivers the electrical signal from the converting means 520 to the electrically controlled module 528 comprised in the second auxiliary means 522, and to the electrically controlled module comprised in the distal part of the optoelectronic probe, such as described with respect to the embodiment of FIG. 4. The splitting and directing means 524 then directs an optical signal returning from the second auxiliary means 522 to the corresponding channel 510 of optical connector means 504. The optical signal returning from the second auxiliary means 522 is thereinafter directed by the directional means 518 to the first auxiliary means 516.

Those skilled in the art will appreciate that the second auxiliary means 522, analogous to that described above with respect to the embodiment of FIG. 3, is capable of providing a unique identification of the optoelectronic probe 506, storing calibration parameters of the optoelectronic probe 506, counting events, such as number of sessions used, time in use, and the like, and communicating this information to the optoelectronic measuring console 502. As will be further recognized by a skilled artisan, the embodiments of the optoelectronic probe system illustrated in FIGS. 3 through 5, when including power level altering means and indicating means (not shown in the drawings) operate analogous to that described above with reference to the embodiment of FIG. 2.

The foregoing description of preferred embodiments of the subject application has been presented for purposes of illustration and description. It is not intended to be exhaustive or to limit the subject application to the precise form disclosed. Obvious modifications or variations are possible in light of the above teachings. The embodiments were chosen and described to provide the best illustration of the principles of the subject application and its practical application to thereby enable one of ordinary skill in the art to use the subject application in various embodiments and with various modifications as are suited to the particular use contemplated. All such modifications and variations are within the scope of the subject application as determined by the appended claims when interpreted in accordance with the breadth to which they are fairly, legally and equitably entitled.

What is claimed:

1. An optoelectronic probe system with all-optical coupling comprising:
   an optoelectronic measuring console;
   optical connector means; and
   an optoelectronic probe in optical communication with the optoelectronic measuring console via the optical connector means, the optoelectronic probe comprising:
      electrically controlled means comprising at least one electrically controlled module,
      transforming means comprised in a proximal part of the optoelectronic probe and adapted for receiving an output optical signal from the optoelectronic measuring console via the optical connector means, the transforming means comprising:
         selecting means adapted for selecting a first optical signal and a second optical signal from the output optical signal received from the optoelectronic measuring console via the optical connector means, and
         converting means optically coupled with the selecting means and adapted for converting at least a part of the first optical signal into an electrical signal,
      first delivering means adapted for delivering the electrical signal from the converting means to the electrically controlled means, and
      second delivering means adapted for delivering the second optical signal to an associated sample,
      wherein the transforming means is further adapted for receiving an optical signal returning from an associated sample via the second delivering means; and
      wherein the transforming means is further adapted for supplying an optical signal representative of the optical signal returning from an associated sample to the optoelectronic measuring console via the optical connector means.

2. The optoelectronic probe system with all-optical coupling of claim 1 wherein the at least one module of the electrically controlled means is selected from the group consisting of scanning module, identification module, and monitoring module.

3. The optoelectronic probe system with all-optical coupling of claim 1 wherein the optoelectronic measuring console comprises:
   a regular optical part;
   a supplemental optical signal source having an operative wavelength other than an operative wavelength of the regular optical part of the optoelectronic measuring console; and
   mixing means in optical communication with the supplemental optical signal source, with the regular optical part of the optoelectronic measuring console, and with the optical connector means;
   wherein the mixing means is adapted for supplying the output optical signal from the optoelectronic measuring console to the optoelectronic probe via the optical connector means, the output signal being representative of the output optical signal from the regular optical part of the optoelectronic measuring console and of the supplemental optical signal;
   wherein the first optical signal selected by the selecting means is representative of the supplemental optical signal; and
   wherein the second optical signal selected by the selecting means is representative of the output optical signal from the regular optical part of the optoelectronic measuring console.

4. The optoelectronic probe system with all-optical coupling of claim 3:
   wherein the optoelectronic measuring console further comprises:
      first auxiliary means adapted for receiving and outputting an auxiliary optical signal, and
      directional means,
      wherein the mixing means is in optical communication with the supplemental optical signal source and with the first auxiliary means via the directional means, and
      wherein the output optical signal from the optoelectronic measuring console supplied by the mixing means to the optoelectronic probe via the optical connector means, is further representative of the auxiliary optical signal;
   wherein the transforming means of the optoelectronic probe further comprises:
      second auxiliary means, and
      splitting and directing means,
      wherein the selecting means is in optical communication with the second auxiliary means and with the converting means via the splitting and directing means,
      wherein the first optical signal selected by the selecting means is further representative of the auxiliary optical signal from the first auxiliary means,
      wherein the splitting and directing means is adapted for splitting the first optical signal into a first part and a second part, directing the first part of the first optical signal to the converting means and directing the second part of the first optical signal to the second auxiliary means, and
      wherein the splitting and directing means is further adapted for directing an optical signal returning from the second auxiliary means to the selecting means.

5. The optoelectronic probe system with all-optical coupling of claim 4 wherein the second auxiliary means comprises at least one module of the electrically controlled means.

6. The optoelectronic probe system with all-optical coupling of claim 4:
   wherein the selecting means is further adapted for mixing the optical signal returning from an associated sample with the optical signal returning from the second auxiliary means; and
   wherein the optical signal being supplied by the transforming means to the optoelectronic measuring console via the optical connector means is further representative of the optical signal returning from the second auxiliary means.

7. The optoelectronic probe system with all-optical coupling of claim 6:
wherein the mixing means is further adapted for receiving from the optoelectronic probe an optical signal supplied by the transforming means via the optical connector means;
wherein the mixing means is further adapted for selecting, from the received optical signal an optical signal representative of the optical signal returning from an associated sample, and selecting an auxiliary optical signal representative of the optical signal returning from the second auxiliary means;
wherein the mixing means is further adapted for directing the optical signal representative of the optical signal returning from an associated sample, to the regular optical part of the optoelectronic measuring console; and
wherein the mixing means is further adapted for directing the optical signal representative of the optical signal returning from the second auxiliary means, to the first auxiliary means via the directional means.

8. The optoelectronic probe system with all-optical coupling of claim 3:
wherein the optoelectronic measuring console further comprises power level altering means in communication with the supplemental optical signal source;
wherein the power level altering means is adapted for lowering the power level of the output optical signal of the supplemental optical signal source to a safe level responsive to a disconnection in the optical connector means; and
wherein the power level altering means is adapted for adjusting the power level of the output optical signal of the supplemental optical signal source to an operative level responsive to a connection in the optical connector means.

9. The optoelectronic probe system with all-optical coupling of claim 8 further comprising indicating means adapted for indicating a status of the optical connector means, wherein the indicating means is in communication with the optoelectronic probe and with the power level altering means.

10. An optoelectronic probe system with all-optical coupling comprising:
an optoelectronic measuring console comprising:
a regular optical part, and
a supplemental optical signal source having an operative wavelength other than an operative wavelength of the regular optical part of the optoelectronic measuring console;
two-channel optical connector means; and
an optoelectronic probe in optical communication with the optoelectronic measuring console via the two-channel optical connector means, wherein the optoelectronic probe is adapted for receiving a first optical signal, representative of a supplemental optical signal from the supplemental optical signal source, and receiving a second optical signal from the regular optical part of the optoelectronic measuring console, via corresponding channels of the two-channel optical connector means, the optoelectronic probe comprising:
electrically controlled means comprising at least one electrically controlled module,
converting means comprised in a proximal part of the optoelectronic probe and adapted for converting at least a part of the first optical signal received by the optoelectronic probe, into an electrical signal,
first delivering means adapted for delivering the electrical signal from the converting means to the electrically controlled means, and
second delivering means adapted for delivering the second optical signal received by the optoelectronic probe to an associated sample, and adapted for delivering an optical signal returning from an associated sample to the optoelectronic measuring console via a corresponding channel of the two-channel optical connector means;
wherein the regular optical part and the supplemental optical signal source of the optoelectronic measuring console are in optical communication with corresponding channels of the two-channel optical connector means.

11. The optoelectronic probe system with all-optical coupling of claim 10 wherein the at least one module of the electrically controlled means is selected from the group consisting of scanning means, identification means, and monitoring means.

12. The optoelectronic probe system with all-optical coupling of claim 10:
wherein the optoelectronic measuring console further comprises:
first auxiliary means adapted for receiving and outputting an auxiliary optical signal, and
directional means,
wherein the supplemental optical signal source and the first auxiliary means are in optical communication with a corresponding channel of the two-channel optical connector means via the directional means, and
wherein the directional means is adapted for directing the auxiliary optical signal from the first auxiliary means and the supplemental optical signal to a corresponding channel of the two-channel optical connector means;
wherein the proximal part of the optoelectronic probe further comprises:
second auxiliary means adapted for receiving and outputting an auxiliary optical signal, and
splitting and directing means,
wherein the converting means and the second auxiliary means are in optical communication with a corresponding channel of the two-channel optical connector means via the splitting and directing means,
wherein the first optical signal received by the optoelectronic probe, is further representative of the auxiliary optical signal output by the first auxiliary means,
wherein the splitting and directing means is adapted for splitting the first optical signal received by the optoelectronic probe, into a first part and a second part, directing the first part of the first optical signal to the converting means, and directing the second part of the first optical signal to the second auxiliary means, and
wherein the splitting and directing means is further adapted for directing an auxiliary optical signal returning from the second auxiliary means to a corresponding channel of the two-channel optical connector means; and
wherein the directional means is further adapted for directing the auxiliary optical signal from the second auxiliary means received via a corresponding channel of the two-channel optical connector means, to the first auxiliary means.

13. The optoelectronic probe system with all-optical coupling of claim 12 wherein the second auxiliary means comprises at least one module of the electrically controlled means.

14. The optoelectronic probe system with all-optical coupling of claim 10:
   wherein the optoelectronic measuring console further comprises power level altering means in communication with the supplemental optical signal source;
   wherein the power level altering means is adapted for lowering the power level of the output optical signal of the supplemental optical signal source to a safe level responsive to a disconnection in the two-channel optical connector means; and
   wherein the power level altering means is adapted for adjusting the power level of the output optical signal of the supplemental optical signal source to an operative level responsive to a connection in the two-channel optical connector means.

15. The optoelectronic probe system with all-optical coupling of claim 14 further comprising indicating means adapted for indicating a status of the two-channel optical connector means, wherein the indicating means is in communication with the optoelectronic probe and with the power level altering means.

* * * * *